United States Patent [19]

Henery et al.

[11] Patent Number: 4,543,438

[45] Date of Patent: Sep. 24, 1985

[54] TERTIARY-BUTYLSTYRENE RECOVERY

[75] Inventors: James D. Henery; Charles L. Edwards; Stephen C. McHaney, all of Odessa, Tex.

[73] Assignee: El Paso Products Company, Odessa, Tex.

[21] Appl. No.: 685,930

[22] Filed: Dec. 24, 1984

[51] Int. Cl.$^4$ ............................................... C07C 7/10
[52] U.S. Cl. ...................................... 585/857; 585/865
[58] Field of Search ............... 585/857, 856, 864, 865

[56] References Cited

U.S. PATENT DOCUMENTS

| | | | |
|---|---|---|---|
| 3,435,087 | 3/1969 | Broughton | 585/857 |
| 3,544,453 | 12/1970 | Thompson | 585/857 |
| 3,558,480 | 1/1971 | Broughton | 585/865 |
| 3,761,403 | 9/1973 | Plummer | 585/865 |
| 4,385,196 | 5/1983 | Carter | 585/857 |

FOREIGN PATENT DOCUMENTS

| | | | |
|---|---|---|---|
| 9135927 | 5/1973 | Japan | 585/857 |
| 0024858 | 2/1979 | Japan | 585/857 |

*Primary Examiner*—D. E. Gantz
*Assistant Examiner*—A. Pal
*Attorney, Agent, or Firm*—Fred S. Valles; Margareta LeMaire

[57] ABSTRACT

The reaction effluent from an oxydehydrogenation reactor, used in the preparation of t-butylstyrene from t-butylethylbenzene, is subjected to liquid-liquid extraction with a sulfolane-water mixture to separate unreacted t-butylethylbenzene from t-butylstyrene.

3 Claims, No Drawings

TERTIARY-BUTYLSTYRENE RECOVERY

BACKGROUND OF THE INVENTION

The invention relates broadly to the manufacture of t-butylstyrene (tBS) by oxidative dehydrogenation (OXD) of t-butylethylbenzene (tBEB) and in particular to the sharp separation of unreacted t-butylethylbenzene feed from t-butylstyrene product.

Tertiary-butylstyrene is a compound which has many uses; e.g., as a chemical intermediate, as a monomer or comonomer in the production of polymeric materials, and the like. Tertiary-butylstyrene has often replaced styrene in some applications because desirable physical and chemical product properties result from such a substitution. In addition, there are processes where styrene is not suitable but where tertiary-butylstyrene functions well.

Because tBS belongs to the same family as styrene, there are similarities in the chemistry of its preparation. One of the common properties is the tendency for the styrenics to polymerize whenever they are activated by chemicals or by heat. Some of the techniques used in purifying styrene can be used to purify tBS. However, because the boiling point of tBS is about 70° C. higher than that of styrene, the tendency for tBS to polymerize is much greater than that of styrene in any of the commercial processes for purifying styrene.

Some of the differences between styrene and tBS derive from the compounds of the dialkenylbenzene family, which are present in tBS but not in styrene. These crosslinking compounds can polymerize to give a type of polymer that interferes with the operation of refining equipment. The crosslinked polymer has a tendency to collect in the equipment and to resist attempts to dissolve it.

Some of the other differences from styrene that arise in the separating of tBS into a pure product derive from the presence of the isomers of tBS and tBEB. Both the meta and para isomers are found in tBEB and tBS. The m-tBS has a boiling point that is intermediate between the boiling points of p-tBEB and p-tBS and is likely to be found in both the top and bottom products if a conventional distillation column were to be used for separating tBEB and tBS.

In copending application Ser. No. 646,266, filed Aug. 31, 1984, an extractive distillation process, has been disclosed for the separation of t-butylstyrene from an OXD reactor effluent containing tBEB and tBS using anhydrous sulfolane as solvent. This process works well; however, the use of reduced pressure and elevated temperature contribute considerably to the equipment, inhibitor, and utilities costs of the overall process.

Trials with anhydrous sulfolane as solvent in liquid/-liquid extraction of OXD reactor effluent indicated that pure tBS could not be produced because anhydrous sulfolane and tBS are completely miscible.

It is, therefore, a principal object of the present invention to provide a separation process utilizing mild operating conditions to obtain a tBS product of acceptable purity from an OXD reactor effluent.

THE INVENTION

In accordance with the present invention, there is provided a process for the separation of t-butylstyrene from an oxidative dehydrogenation reactor effluent containing t-butylethylbenzene and t-butylstyrene comprising: introducing said effluent as feed to a liquid/liquid extraction zone; intimately contacting said feed in said zone with aqueous sulfolane containing from about 2 to about 10 wt. % water; recovering t-butylethylbenzene as raffinate; and recovering an extract containing t-butylstyrene.

The feed should preferably contain a polymerization inhibitor effective in supressing polymerization of tBS and aromatic dialkenyl compounds. Suitable inhibitors include tertiary-butyl catechol, 2,4-dinitrophenol and 2,6-dinitro-m-cresol. The concentration of inhibitor in the feed to the column should range between about 25 and about 1,000 ppm by weight.

The operating conditions used in the process are generally mild. Atmospheric pressure and ambient temperatures, from about 20° C. to about 40° C., are usually employed; although it is entirely within the scope of the invention to employ both higher and lower temperatures, if so desired. For best separation results, it is preferred that when temperatures in the aforementioned upper range are used in the separation, the water content of the aqueous sulfolane solvent is also adjusted upwards within its disclosed range. The solvent-to-feed weight ratio should be maintained in a range from about 4:1 to about 30:1. Reflux can be provided to the extract end of the extraction zone to increase separation of the tBS from tBEB. The extract reflux, which is provided by returning a portion of the extract from which the solvent has been removed, should be maintained between about 8:1 and about 50:1.

Any efficient liquid/liquid contacting apparatus may be used for the extraction process of this invention. Countercurrent devices such as mixer-settler extractors, spray or packed columns, bubble-cap columns, sieve or perforated-tray columns, and the like can be used.

In the operation of the liquid/liquid extraction it is possible to obtain a tBEB raffinate containing only small amounts of tBS; e.g., less than 0.5 wt. %. The raffinate will also contain small amounts of sulfolane, usually in the range from about 5 to about 10 wt. %. The sulfolane is removed by a water washing treatment and the washed tBEB containing, at most, traces of sulfolane is now suitable to be returned as feed to OXD reactor used in the manufacture of tBS.

The extract contains the aqueous sulfolane solvent, the tBS and very small quantities of tBEB: typically less than about 2 wt. %. In addition, the extract contains dialkenyl aromatic impurities and higher boiling hydrocarbons introduced with the feed to the extraction. The tBS product is recovered in any suitable fashion; e.g., by mixing the extract with water, which causes a dilution of the sulfolane and a separation of a hydrocarbon layer which includes most of the tBS and some of the impurities. After decantation and further washing of the hydrocarbon phase to remove residual sulfolane, the hydrocarbon stream is advantageously fed to a distillation zone where higher-boiling impurities are removed from the tBS. If desired, the tBS product can be purified further; e.g., by the extractive distillation method disclosed and claimed in copending application Ser. No. 646,267 filed Aug. 31, 1984, or by the liquid/liquid extraction method of copending application Ser. No. 685,929 filed Dec. 24, 1984. The aqueous sulfolane is distilled to give a sulfolane stream for recycle containing the desired concentration of water for reuse within the overall process.

The following examples illustrate the invention but are not intended to limit its scope.

EXAMPLE 1

A crude tBS made by OXD of tBEB was subjected to countercurrent liquid/liquid extraction using a York-Scheibel Model XA-1 column extractor containing 11 mixer-settler stages. The column was 1" diameter × 48" tall. The mixer sections were 0.5" with a 3" settling zone. The initial experiments were conducted by feeding hydrocarbon into the bottom and solvent into the top. The solvent was the continuous phase. Raffinate was taken from the top of the column and extract from the bottom.

The hydrocarbon feed (65.3 wt. % tBEB and 33.4 wt. % tBS) was fed at the bottom of the column at the rate of 5.0 ml/min and sulfolane containing 3 wt. % water was fed at the top of the column at 25.1 ml/min. The mixer stirring rate was 600 rpm. Extract taken off the bottom of the column at a rate of 29.3 ml/min was richer in tBS on a solvent-free basis, and the raffinate recovered at a rate of 0.5 ml/min was purer in tBEB on a solvent-free basis, as is shown by the data in Table I.

TABLE I

| COMPOSITION OF EXTRACT AND RAFFINATE (Wt. %) | | | | |
|---|---|---|---|---|
| Component | Extract | Raffinate | Extract[1] | Raffinate[1] |
| tBEB | 5.6 | 94.3 | 57.1 | 98.8 |
| tBS | 4.0 | 0.7 | 41.6 | 0.8 |
| Sulfolane | 90.2 | 4.7 | — | — |

[1]Solvent Free Basis

EXAMPLES 2-4

These examples demonstrate that tBS can be obtained substantially free of tBEB and approximate what would occur in a column of sufficient length using a reflux stream of 99.8 wt. % tBS.

In Example 2 the extract from Example 1 was used as solvent and the hydrocarbon in this experiment was 99.8 wt. % tBS. The average hydrocarbon feed rate was 5.1 ml/min, the average solvent feed rate was 25.3 ml/min, the raffinate take-off rate was 1.2 ml/min, and that of the extract about 29.3 ml/min. The results are shown in Table II.

TABLE II

| COMPOSITION OF EXTRACT AND RAFFINATE (Wt. %) | | | | |
|---|---|---|---|---|
| Component | Extract | Raffinate | Extract[1] | Raffinate[1] |
| tBEB | 2.78 | 64.7 | 11.4-14.2 | 70.7-71.0 |
| tBS | 16.8 | 27.0 | 85.8-88.1 | 28.6-29.0 |
| Sulfolane | 80.3 | 7.7 | — | — |

[1]Solvent Free Basis

The extract from Example 2 was used in Example 3 as solvent. The hydrocarbon used was 99.8% tBS, which was fed at a rate of 4.1-4.5 ml/min. The solvent feed rate was 19.3-24.7 ml/min, the raffinate rate was 1.7-2.3 ml/min, and the extract rate was 21-22 ml/min. The mixer stirring rate was about 100 rpm. Table III gives the results of this experiment.

TABLE III

| COMPOSITION OF EXTRACT AND RAFFINATE (Wt. %) | | | | |
|---|---|---|---|---|
| Component | Extract | Raffinate | Extract[1] | Raffinate[1] |
| tBEB | 0.63-1.03 | 12.6-15.0 | 2.41-4.01 | 15.5-18.9 |
| tBS | 24.1-26.0 | 60.6-64.5 | 95.5-97.3 | 74.4-80.9 |
| Sulfolane | 23.5-25.3 | 18.5-20.6 | — | — |

[1]Solvent Free Basis

The extract from Example 3 was used in Example 4 as solvent in a further experiment. The hydrocarbon used was 99.8% tBS. The hydrocarbon feed rate was 4.0 ml/min, the solvent feed rate was 20.5-20.9 ml/min, the raffinate rate was 3-4 ml/min, and the extract rate was 21-20 ml/min, The results are shown in Table IV.

TABLE IV

| COMPOSITION OF EXTRACT AND RAFFINATE (Wt. %) | | | | |
|---|---|---|---|---|
| Component | Extract | Raffinate | Extract[1] | Raffinate[1] |
| tBEB | 0.41-0.56 | 4.60-5.03 | 1.61-1.93 | 6.26-6.78 |
| tBS | 26.3-28.4 | 68.6-68.9 | 97.5-98.1 | 92.9-93.4 |
| Sulfolane | 71.0-73.2 | 25.8-26.5 | — | — |

[1]Solvent Free Basis.

EXAMPLE 5

The following is a calculated example in which the feed stream of Example 1 is contacted at atmospheric pressure and about 25 C with an aqueous sulfolane solvent containing about 3 wt. % water in a liquid/liquid extraction column having 25 theoretical stages. A solvent-to-feed ratio of 26:1 is employed. A solute ratio of 14:1 is provided at the extract end. The pertinent data are shown in Table V.

TABLE V

| COMPOSITION OF EXTRACT AND RAFFINATE (Wt. %) | | | | |
|---|---|---|---|---|
| Component | Extract | Raffinate | Extract[1] | Raffinate[1] |
| tBEB | 0.8 | 88.8 | 2.0 | 95.0 |
| tBS | 6.0 | 4.7 | 98.0 | 5.0 |
| Sulfolane | 93.2 | 6.5 | — | — |

[1]Solvent Free Basis

It is obvious to those skilled in the art that many variations and modifications may be made without departing from the spirit and scope of the invention as herein described and defined in the appended claims.

What is claimed is:

1. A process for the separation of t-butylstyrene from an oxidative dehydrogenation zone effluent containing t-butylethylbenzene and t-butylstyrene comprising:
   introducing said effluent as feed to a liquid/liquid extraction zone;
   intimately contacting said feed in said zone with aqueous sulfolane solvent containing from about 2 to about 10 wt. % water;
   recovering t-butylethylbenzene as raffinate, and recovering an extract containing t-butylstyrene.

2. The process of claim 1 wherein the solvent to feed ratio is maintained in a range from about 4:1 to about 30:1.

3. The process of claim 1 wherein a portion of the extract after removal of sulfolane solvent is refluxed to the extract end of the extraction zone to provide a reflux ratio in the range between about 8:1 and about 50:1.

* * * * *